United States Patent [19]

Park

[11] Patent Number: 5,137,507
[45] Date of Patent: Aug. 11, 1992

[54] MAGNETIC RING FOR STIMULATING FINGERS OR TOES

[76] Inventor: Chang-Wan Park, 8-5, 2-Ka, Myungruin-Dong, Chongro-Ku, Seoul, Rep. of Korea

[21] Appl. No.: 645,437
[22] Filed: Jan. 24, 1991
[51] Int. Cl.$^5$ ................................................ A61N 1/00
[52] U.S. Cl. ..................................... 600/13; 128/907; 600/9
[58] Field of Search ................ 600/9, 13, 15; 128/907

[56] References Cited

FOREIGN PATENT DOCUMENTS 3403094  8/1985  Fed. Rep. of Germany .......... 600/9
1245315  7/1986  U.S.S.R. ................................... 600/9

Primary Examiner—Richard J. Apley
Assistant Examiner—Susan L. Weinhoffer
Attorney, Agent, or Firm—Armstrong, Nikaido, Marmelstein, Kubovcik & Murray

[57] ABSTRACT

The purpose of this invention is to provide a magnetic ring for stimulating the correspondence part at the fingers or toes using the pressing, magnetic and metalionic effects of the ring. The magnetic ring of this invention comprises a multi-angled and coiled string which presses the fingers by its elasticity, a round magnet which is inserted in the coiled string to give the magnetic effects to the fingers or toes, and means for connecting both ends of the coiled string in order to make a round shape of the ring.

5 Claims, 2 Drawing Sheets

MAGNETIC RING FOR STIMULATING FINGERS OR TOES

BACKGROUND OF THE INVENTION

This invention relates to a novel magnetic ring which stimulates the corresponding part of the weak human body, more specifically, to a magnetic ring which cures the diseases by stimulating the corresponding part at the fingers or toes using the pressing, magnetic and metal-ionic effects of the ring.

DESCRIPTION OF THE PRIOR ART

One of the characteristics of the human body is an existence of a correspondence system between the whole body and some of its parts. Above mentioned characteristics of the human body were discovered by Dr. P. Nogier, a French neurologist, in the course of using the auricular needle therapy on his patients in 1956. Through this treatment, he confirmed that only an acupuncture to the ear can affect the whole body, according to the correspondence system.

In Korea, many attempts for curing the diseases by acupuncture to the hand or foot have been tried on the supposition that there exists a body correspondence between the hand or foot and the whole body. Actually, many patients have been cured by this acupuncture to the hand or foot.

In 1988, the book "Guide to hand nd foot acupuncture" which describes the theories and therapeutic applications of a body correspondence system was published by the inventor in Korea.

In this publication, the theory of a correspondence reaction, that is, if one part of the human body is ill, it brings a correspondence reaction to hand or foot, is well described and the stimulation of this correspondence part of hand or foot is recommended for curing the diseases. For the better understanding of the human correspondence system, the important figures of this book are illustrated as FIG. 10 and 11.

Acupuncture is generally used for stimulating the corresponding part of the hand or foot. But it is not easy for the ordinary person to sting the Correspondence Point without aids of the oriental doctor.

SUMMARY OF THE INVENTION

The purpose of this invention is to provide a magnetic ring which cures the diseases by stimulating the correspondence part at the fingers or toes using the pressing, magnetic and metal-ionic effects of the ring. The magnetic ring of this invention comprises a multi-angled and coiled string, which presses the fingers by its elasticity, a round magnet which is inserted in the coiled string to give the magnetic effects to the fingers or toes and means for connecting both ends of the coiled string in order to make a round shape of the ring.

DETAILED DESCRIPTION OF THE PREFERRED EMBODIMENT

Figure 1:
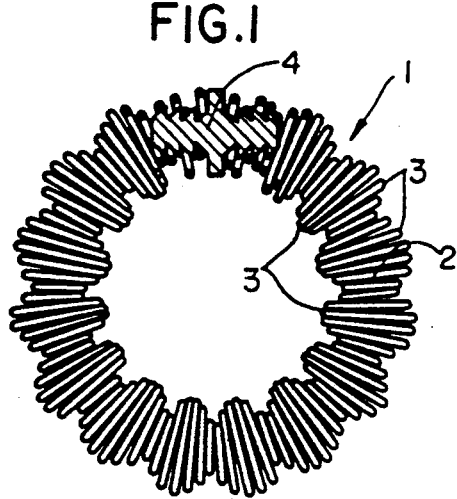
FIG. 1 is a partially cutaway view in front of a preferred embodiment of this invention.

As shown in FIG. 1, the appearance of a magnetic ring 1 of this invention has a shape of coiled string which is twisted and closely stacked.

Figure 2:
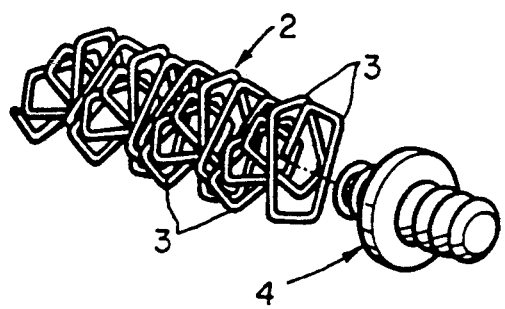
FIG. 2 shows a multi-angle shape of coiled string and means for connecting it of this invention.

The detailed structure of this coiled string 2 can be explained by FIG. 2, which illustrates the multi-angled and coiled string and the means for connecting it 4.

This coiled string is wound into a multi-angle shape, and the angles 3 of which give the effective pressure to the finger. The coiled string is normally made from steel or steel alloy, which is suitable for giving the metal-ionic effect to the fingers.

As shown in FIG. 1 and FIG. 2, the means for connecting both ends of the coiled string 4 is provided so that the coiled string can be used as a ring.

Figure 3:
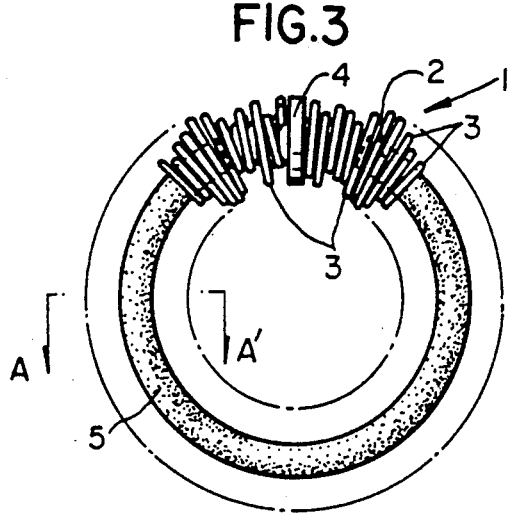
FIG. 3 is a partially cutaway view in order to show one example of the magnet.

The magnet is inserted in the coiled string in order to give a magnetic effect to the fingers. The FIG. 3 illustrates one example of magnet, a rubber magnet 5 which is made from the mixture of rubber and magnetic ferrous oxide.

Figure 4:
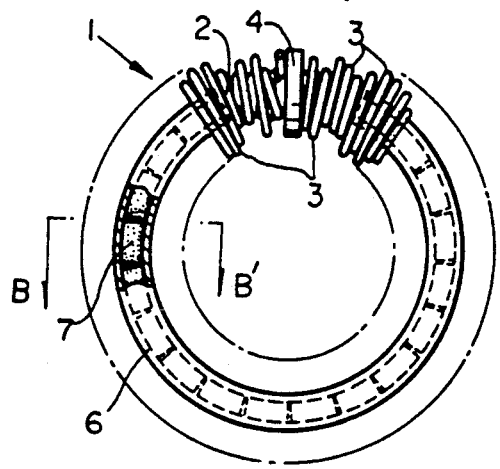
FIG. 4 is a partially cutaway view in order to show another example of the magnet.

The FIG. 4 illustrates another example of magnet, a plurality of small magnets 7 inserted in a thin tube 6.

Figure 5:
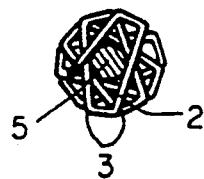
FIG. 5 is a sectional view taken along the line A-A' of FIG. 3.
Figure 6:
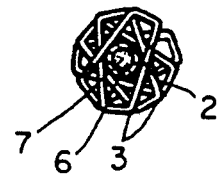
FIG. 6 is a sectional view taken along the line B—B' of FIG. 4.
Figure 7:
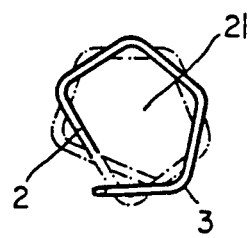
FIG. 7 shows an example of multi-angle shape of coiled string.

The FIG. 5 and FIG. 6 show the sectional view taken along the lines A—A' and B—B' respectively.

Figure 8:
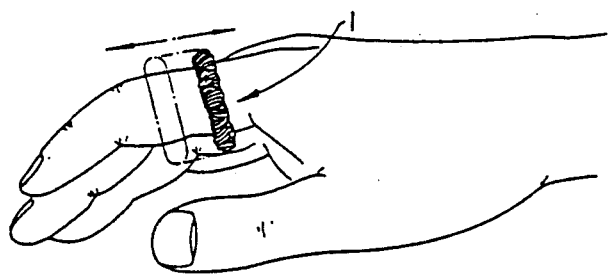
FIG. 8 shows an example for stimulating the fingers using the magnetic ring of this invention.
Figure 9:
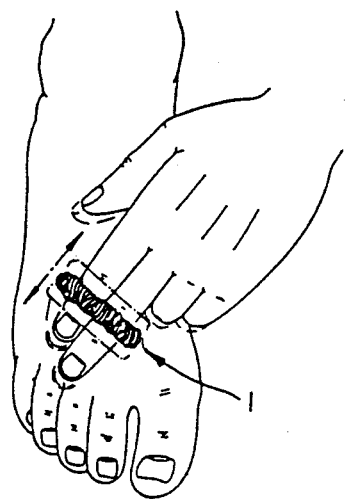
FIG. 9 shows an example for stimulating the toes using the magnetic ring of this invention.

In order to stimulate the fingers or toes, the magnetic ring of this invention can be used the way shown in FIG. 8 and FIG. 9.

As shown in FIG. 8, after wearing the ring at the finger, the user stimulates the correspondence part of the human body by rolling the ring in order to give the pressing, magnetic and metal-ion effects to the finger.

FIG. 9 illustrates another usage of this ring in order to stimulate the toes or foot, with which the user can rub the toes or foot.

The therapeutic effects of this ring depends on the correct usage of this ring, which requires the appropriate stimulation to the correspondence part of the weak human body.

Figure 10:
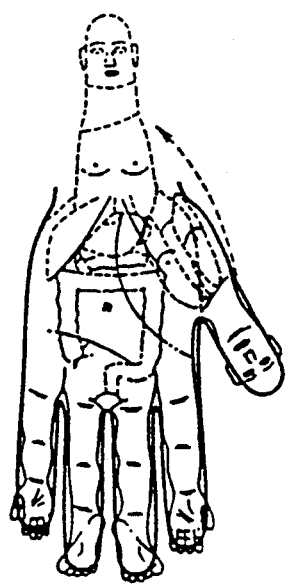
FIG. 10 shows a body correspondence system between hand and whole body.
Figure 11:
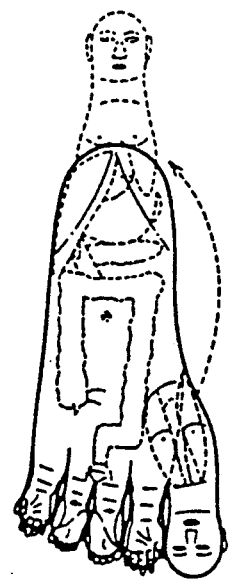
FIG. 11 shows a body correspondence system between foot and whole body.

For this purpose, FIG. 10 and FIG. 11 will be helpful for searching the correspondence part of the human body.

I claim:

1. A magnetic ring for stimulating the correspondence part at the fingers or toes comprising;
    a multi-angled and coiled string which presses the fingers by its elasticity;
    a round magnet which is inserted in the coiled string to give magnetic effects to the fingers or toes; and
    means for connecting both ends of the coiled string in order to make a round shape of the ring.

2. A magnetic ring according to claim 1 wherein the magnet is a rubber magnet which is made from the mixture of rubber and magnetic ferrous oxide.

3. A magnetic ring according to claim 1 wherein the magnet is a plurality of small magnets inserted in thin tube.

4. A magnetic ring according to claim 1 wherein said multi-angled string is a rectangular shape.

5. A magnetic ring according to claim 1 wherein the coiled string is made from steel or steel alloy.

* * * * *